United States Patent [19]

Westermann et al.

[11] 4,013,663
[45] Mar. 22, 1977

[54] ISOQUINOLINE COMPOUNDS

[75] Inventors: Albert Westermann, Ludwigshafen (Rhine); Frank Zimmermann, Neustadt-Haardt; Dirk Wuppermann, Freinsheim; Ludwig Friedrich, Bruehl; Manfred Raschack, Weisenheim am Sand, all of Germany

[73] Assignee: Knoll A.G. Chemische Fabriken, Ludwigshafen (Rhine), Germany

[22] Filed: Oct. 30, 1975

[21] Appl. No.: 627,291

[30] Foreign Application Priority Data

Nov. 15, 1974  Germany .......................... 2454198
Apr. 30, 1975  Germany .......................... 2519163

[52] U.S. Cl. .......................... 260/287 D; 424/258; 260/288 D
[51] Int. Cl.² ............................ C07D 217/04
[58] Field of Search ............ 260/288 D, 287 D; 424/258

[56] References Cited

UNITED STATES PATENTS

| | | | |
|---|---|---|---|
| 3,340,266 | 9/1967 | Howe et al. | 260/288 R |
| 3,910,924 | 10/1975 | Tamura et al. | 260/288 R |

FOREIGN PATENTS OR APPLICATIONS 1,058,822  2/1967  United Kingdom ............ 260/288 R

*Primary Examiner*—Donald G. Daus
*Assistant Examiner*—Mary C. Vaughn
*Attorney, Agent, or Firm*—Curtis, Morris & Safford

[57] ABSTRACT

Isoquinoline compounds having β-receptor blocking activity, particularly for the heart, and having the formula

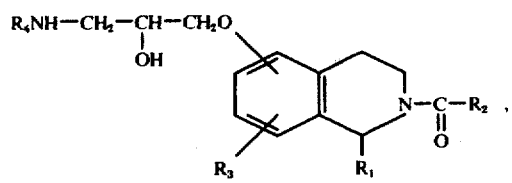

and salts thereof with physiologically tolerable acids, wherein $R_1$ is hydrogen or methyl, $R_2$ is hydrogen or lower alkyl, $R_3$ is hydrogen or methoxy, and $R_4$ is isopropyl or tertiary butyl. A method for making such compounds. Pharmaceutical compositions containing such compounds.

27 Claims, No Drawings

ISOQUINOLINE COMPOUNDS

The present invention relates to certain isoquinoline compounds, to a method for making the same, and to pharmaceutical compositions containing said compounds.

A number of substances which block β-receptors, i.e. which occupy β-receptors without exciting them, are known. However, these compounds have the disadvantage that the β-blocking activity either is not specific to an organ or that their tolerability is not optimal. That is, their therapeutic index, or the difference between the therapeutically-effective dose and the toxic dose, is not very large.

The present invention relates more in particular to isoquinoline derivatives of the formula

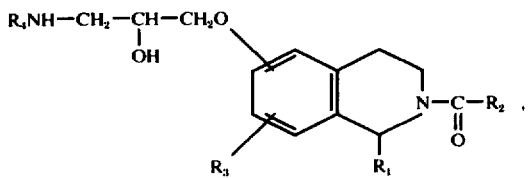

in which $R_1$ is hydrogen or methyl, $R_2$ is hydrogen or lower alkyl, $R_3$ is hydrogen or methoxy, and $R_4$ is isopropyl or tertiary butyl, as well as to salts of these compounds with physiologically tolerable acids.

The invention also relates to a process for the preparation of compounds of the formula given above, which process comprises reacting a compound of the formula

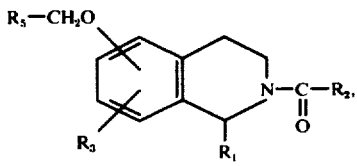

in which $R_1$, $R_2$, and $R_3$ have the same meaning as above, and $R_5$ is

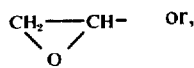

or,

$Hal-CH_2-CHOH-$, wherein Hal is a halogen atom, with an amine of the general formula $R_4NH_2$, in which $R_4$ has the above-mentioned meaning, and the compounds so obtained are optionally converted into their salts with physiologically tolerable acids.

The reaction according to the invention can be carried out in the presence or absence of a solvent. Suitable solvents are, for example, lower alcohols having 1 to 4 carbon atoms, preferably isopropanol. The reaction is preferably carried out at the boiling point of the solvent. However, it also occurs at room temperature.

The heretofore-unknown epoxy- and chlorohydrin-compounds which serve as starting materials for the preparation of the substances of the invention can be prepared in a known fashion by the reaction of the corresponding isoquinoline derivatives with epichlorohydrin, as shown hereinafter in detail.

The new compounds can be used as such or in the form of their salts with physiologically tolerable acids. Such acids are, for example, hydrochloric acid, sulfuric acid, phosphoric acid, acetic acid, malonic acid, succinic acid, citric acid, tartaric acid, lactic acid, diamidosulfonic acid, mucic acid, and maleic acid.

The new compounds are characterized by a high β-receptor blocking activity and a low toxicity. The β-receptor blocking activity can be demonstrated on the β-receptors of the heart, the blood vessel system, and the bronchial system. In part, the new substances especially block the β-receptors of the heart, which can be of significance in the field of use for which the new substances are proposed.

The particular β-receptor blocking activity on the heart in comparison to that on the blood vessel system was measured by the taking of an EKG or by measurement of the blood pressure in the same animal (guinea pigs) [cf. J. R. C. Baird et al., J. Pharm. Pharmac. 24, 880 – 885 (1972) and H. R. Kaplan et al., J. Pharmacol. Exp. Ther. 185, 395 – 405 (1973)]. For investigation of broncho-constrictor activity, the inhibition of the isoprenalin effect on the bronchial system of the guinea pig is employed [cf. H. Konzett et al., Arch. exp. Path. Pharmak. 195, 71 – 74 (1940)]

The following new compounds were examined:
2-acetyl-1,2,3,4-tetrahydro-6-(2-hydroxy-3-isopropylamino-propoxy)-isoquinoline (A),
2-acetyl-1,2,3,4-tetrahydro-6-(2-hydroxy-3-isopropylamino-propoxy)-7-methoxy-isoquinoline (B)
2-formyl-1,2,3,4-tetrahydro-5-(2-hydroxy-3-isopropylamino-propoxy)-isoquinoline (C)
2-formyl-1,2,3,4-tetrahydro-5-(2-hydroxy-3-tert.-butylaminopropoxy)-isoquinoline (D).

Comparison compounds were:
prindolol (E)
propranolol (F)
practolol (B).

Following Table 1 gives the experimentally determined intravenous doses (effective dose on the β-receptors of the heart, blood vessel system, and bronchial system = ED — heart, ED — blood vessel system, ED bronchial system of A, and B in comparison with F.

Table 1

| Substance | ED - Heart | | ED Blood Vessels | | ED Bronchial System | |
|---|---|---|---|---|---|---|
| A | 13 | mg/kg | 80 | mg/kg | 71 | mg/kg |
| B | 5.5 | " | 10 | " | >40 | " |
| F | 1.2 | " | 1.2 | " | 0.18 | " |

From the Table, the following activity relationships for these substances are evident.

Table 2

| Substance | Heart: Blood vessels | Heart: Bronchial System |
|---|---|---|
| A | 1: 6.2 | 1: 5.5 |
| B | 1: 1.8 | 1: >7.2 |
| F | 1: 1 | 1: 0.15 |

It is evident that the dosage relationships for A and B are essentially more favorable than for the comparison compound. This is particularly true for the relationship of the heart-active to the bronchial system-active dose, i.e. the administration of heart-active doses does not lead to a negative influence on the bronchial system.

Following Table 3 shows the superiority of the new substances in comparison with known compounds from the viewpoint of the ratio of efficacy to toxicity. The values in column I correspond to those in Table 1/ED — heart. However, the values are generally lower since the animals were pre-treated with reserpine. The investigations on toxicity were carried out by intravenous administration to albino mice. The values obtained are given in column II.

Table 3

| Substance | I<br>ED - Heart | | II<br>$LD_{50}$ | |
|---|---|---|---|---|
| C | 0.18 | mg/kg | 148 | mg/kg |
| D | 0.041 | " | 128 | " |
| E | 0.071 | " | 22.6 | " |
| F | 0.33 | " | 24.4 | " |
| G | 4.37 | " | 121 | " |

Table 3 shows that C and D are less toxic at higher activity, i.e. that in comparison with compounds E, F, and G they show an essentially more beneficial relationship of the effective dose to the toxic dose. The ratios $LD_{50}:ED_{50}$ for the new compounds are of the order of magnitude of about 800 to over 3000, whereas those for the comparison compounds are, on the other hand, from about 30 to somewhat over 300.

The new compounds are useful for the treatment of functional heart ailments such as tachycardia or palpitation, tachycardiac disturbances of the heart rhythm, extrasystoles, angina pectoris, hyperkinetic heart syndrome, and for other disturbances, as well as for hypertonia.

As administration forms, tablets, capsules, and perorally or parenterally administrable solutions are suitable. For peroral applications, about 1–200 mg per patient per day and, for intravenous applications, about 0.1–20 mg per patient per day, are used.

A better understanding of the present invention and of its many advantages will be had by referring to the following specific examples, given by way of illustration.

Preparation of the heretofore-unknown starting compounds.

A. N-Acyl-isoquinoline-derivatives.

a. 46.0 g of 1,2,3,4-tetrahydro-6-hydroxy-isoquinoline-hydrobromide are reacted with 85 ml of formamide for 1 hour at 140° C. with stirring. After cooling to 100° C., 216 ml of water are added, whereby the reaction product crystallizes. 34.0 g of 2-formyl-1,2,3,4-tetrahydro-6-hydroxy-isoquinoline are obtained. m.p. = 185.5° – 186° C. (ethanol).

In the same manner is prepared:
2-formyl-1,2,3,4-tetrahydro-6-hydroxy-7-methoxy-isoquinoline, m.p. = 172.5° – 174° C.

b. A mixture of 57.6 g of 1,2,3,4-tetrahydro-6-hydroxy-isoquinoline-hydrobromide, 22.6 g of anhydrous sodium acetate, and 76.6 g of acetic acid anhydride in 300 ml of methylene chloride is held at the boiling point for one hour under reflux. 300 ml of water are added thereto, the organic phase is separated, and the aqueous phase is extracted several times with methylene chloride. After evaporation of the methylene chloride extract, the residue is dissolved in dilute sodium hydroxide, stirred for 30 minutes on a boiling water bath, and the reaction product is precipitated by the introduction of carbon dioxide. The filtered substance is recrystallized from ethanol. 43.5 g of 2-acetyl-1,2,3,4-tetrahydro-6-hydroxy-isoquinoline are obtained. m.p. = 135° – 136° C. (ethanol - diisopropyl ether).

In the same manner is prepared:
2-acetyl-1,2,3,4-tetrahydro-6-hydroxy-1-methyl-isoquinoline, m.p. = 161° – 162° C.

c. 55.5 g of propionyl chloride are added dropwise at room temperature over a period of one hour to a mixture of 86.3 g of 1,2,3,4-tetrahydro-6-hydroxy-7-methoxy-isoquinoline-hydrochloride, 138,2 g of potassium carbonate, 600 ml of methylene chloride, and 480 ml of water. The mixture is stirred for an additional 18 hours, the organic phase is separated, and the aqueous phase is extracted twice with methylene chloride. The methylene chloride extracts are dried and evaporated. 65.8 g of 1,2,3,4-tetrahydro-6-hydroxy-7-methoxy-2-propionyl-isoquinoline are obtained. m.p. = 116° – 118° C. (ethyl acetate - diisopropyl ether).

d. 122.3 g of 5-benzyloxy-1,2,3,4-tetrahydro-6-methoxy-isoquinoline-hydrochloride, 140 ml of formic acid, and 700 ml of formamide are heated for 2.5 hours under reflux. The mixture is then poured over 2 kg of ice and extracted with methylene chloride. After evaporation to dryness of the methylene chloride solution under reduced pressure, the residue is recrystallized from methanol-water. 102.3 g of 5-benzyloxy-2-formyl-1,2,3,4-tetrahydro-6-methoxy-isoquinoline are obtained. m.p. = 117.5° – 118.5° C.

89.2 g of 5-benzyloxy-2-formyl-1,2,3,4-tetrahydro-6-methoxy-isoquinoline are dissolved in 450 ml of glacial acetic acid and hydrogenated at room temperature and normal pressure in the presence of 4.5 g of 5 percent palladium black. After conclusion of hydrogen absorption, the reaction mixture is separated from the catalyst by filtration and evaporated to dryness under reduced pressure. Recrystallization of the residue from ethanol gives 57.2 g of 2-formyl-1,2,3,4-tetrahydro-5-hydroxy-6-methoxy-isoquinoline. m.p. = 172.5° – 173.5° C.

In the same manner is prepared:
2-formyl-1,2,3,4-tetrahydro-6-hydroxy-7-methoxy-1-methyl-isoquinoline. m.p. = 175° – 176° C.

e. A mixture of 122.3 g of 5-benzyloxy-1,2,3,4-tetrahydro-6-methoxy-isoquinoline-hydrochloride, 36.1 g of sodium acetate, 81.7 g of acetic anhydride, and 500 ml of methylene chloride is stirred for 1 hour at the boiling point. After cooling, the mixture is combined with 500 ml of water and the organic phase is separated and evaporated to dryness under reduced pressure. 99.5 g of 2-acetyl-5-benzyloxy-1,2,3,4-tetrahydro-6-methoxy-isoquinoline are obtained. m.p. = 94° – 95° C. (ethyl acetate - diisopropyl ether).

After debenzylation according to (d) 58.4 g of 2-acetyl-1,2,3,4-tetrahydro-5-hydroxy-6-methoxy-isoquinoline are obtained. m.p. = 186° –187.5° C.

B. (3-Chloro-2-hydroxy-propoxy)- and (2,3-epoxy-propoxy)-N-acyl-isoquinoline-derivates.

a. A solution of 6.8 g of sodium hydroxide in 90 ml of water is added dropwise over 1 hour to a mixture of 26.6 g of 2-formyl-1,2,3,4-tetrahydro-6-hydroxy-isoquinoline and 42.5 g of epichlorohydrin at 60° C. The reaction mixture is held at this temperature for an additional hour, then allowed to cool and extracted several times with methylene chloride. The organic phase, dried over sodium sulfate, is evaporated and the residue is rubbed with diethyl ether. 29.0 g of 6-(2,3-epoxy-propoxy)-2-formyl-1,2,3,4-tetrahydro isoquinoline are obtained. m.p. = 78° – 79° C. (ethyl acetate - diethyl ether).

In the same manner are prepared:

2-acetyl-6-(2,3-epoxy-propoxy)-1,2,3,4-tetrahydro-isoquinoline, m.p. = 69° – 70° C. (ethyl acetate - diethyl ether).

6-(2,3-epoxy-propoxy)-2-formyl-1,2,3,4-tetrahydro-7-methoxy-isoquinoline, m.p. = 121° – 121.5° C. (ethyl acetate).

2-acetyl-6-(2,3-epoxy-propoxy)-1,2,3,4-tetrahydro-7-methoxy-isoquinoline, m.p. = 111° – 112° C. (ethyl acetate - diisopropyl ether).

6-(2,3-epoxy-propoxy)-1,2,3,4-tetrahydro-7-methoxy-2-propionyl-isoquinoline, m.p. = 67° – 68° C. (diethyl ether).

2-acetyl-6-(2,3-epoxy-propoxy)-1,2,3,4-tetrahydro-7-methoxy-1-methyl-isoquinoline, m.p. = 124° C. (ethylacetate - diisopropylether).

2-formyl-5-(2,3epoxy-propoxy)1,2,3,4-tetrahydro-6-methoxy-isoquinoline, m.p. = 67° – 68° C. (diethyl ether).

2-acetyl-5-(2,3-epoxy-propoxy)-1,2,3,4-tetrahydro-6-methoxy-isoquinoline, m.p. = 86.5° – 87° C. (ethyl acetate - diisopropyl ether)

2-acetyl-6-(2,3-epoxy-propoxy)-1,2,3,4-tetrahydro-7-methoxy-1-methyl-isoquinoline, m.p. = 119° – 123° C. (ethyl acetate - diisopropyl ether).

2-acetyl-7-(2,3-epoxy-propoxy)-1,2,3,4-tetrahydro-isoquinoline, m.p. = 80.5° – 82° C. (ethyl acetate - diisopropyl ether)

b. A mixture of 22.1 g of 2-acetyl-1,2,3,4-tetrahydro-6-hydroxy-7-methoxy-isoquinoline, 27.8 g of epichlorohydrin, and 0.2 ml of piperidine is reacted with stirring for 18 hours at 100° C. After evaporation to dryness under reduced pressure, the residue is taken up in 75 ml of chloroform, hydrogen chloride is introduced, and the mixture is again evaporated to dryness. The thus obtained 2-acetyl-6-(3-chloro-2-hydroxy-propoxy)-1,2,3,4-tetrahydro-7-methoxy-isoquinoline is direcrhy used for Example 4.

c. A solution of 13.6 g of sodium hydroxide in 180 ml of water is added dropwise over one hour to a mixture of 53.2 g of 2-formyl-1,2,3,4-tetrahydro-5-hydroxy-isoquinoline and 83.3 g of epichlorohydrin at 60° C. The reaction mixture is held for an additional hour at this temperature, allowed to cool, and extracted several times with methylene chloride. The organic phase, dried over sodium sulfate, is evaporated and the residue is purified by column chromatography over damp silica gel (11.5 percent water). By elution with a mixture of chloroformethyl acetate (30:1) and evaporation, 59.7 g of 5-(2,3-epoxy-propoxy)-2-formyl-1,2,3,4-tetrahydro-isoquinoline are obtained as a colorless oil.

In the same manner as prepared:

2-acetyl-5-(2,3-epoxy-propoxy)-1,2,3,4-tetrahydro-isoquinoline, colorless oil.

2-acetyl-6-(2,3-epoxy-propoxy)-1,2,3,4-tetrahydro-1-methyl-isoquinoline, colorless oil.

2-formyl-6-(2,3-epoxy-propoxy)-1,2,3,4-tetrahydro-7-methoxy-1-methyl-isoquinoline, m.p. = 101° – 102.5° C. (ethyl acetate - diethyl ether).

2-formyl-8-(2,3-epoxy-propoxy)-1,2,3,4-tetrahydro-7-methoxy-isoquinoline, m.p. = 73° – 74° C. (ethyl acetate - diisopropyl ether).

2-acetyl-8-(2,3-epoxy-propoxy)-1,2,3,4-tetrahydro-7-methoxy-isoquinoline, colorless oil.

Preparation of the final products.

EXAMPLE 1

A mixture of 24.7 g of 2-acetyl-6-(2,3-epoxy-propoxy)-1,2,3,4-tetrahydro-isoquinoline and 73,1 g of tertiary butylamine is boiled under reflux for 72 hours. The mixture is evaporated to dryness under reduced pressure and the residue is taken up in diethyl ether. After cooling and filtration, 25.1 g of 2-acetyl-1,2,3,4-tetrahydro-6-(2-hydroxy-3-tert.-butylamino-propoxy)-isoquinoline are obtained. m.p. = 74° – 75° C. (ethyl acetate-diethyl ether).

In the same manner are prepared:

2-acetyl-1,2,3,4-tetrahydro-6-(2-hydroxy-3-tert.-butylamino-propoxy)-7-methoxy-isoquinoline, m.p. = 97° C. (ethyl acetate - diisopropyl ether). Yield: 85 percent of theory.

2-formyl-1,2,3,4-tetrahydro-5-(2-hydroxy-3-tert.-butylamino-propoxy)-6-methoxy-isoquinoline, m.p. = 67° – 68° C. (diethyl ether - diisopropyl ether). Yield: 85 percent of theory.

2-acetyl-1,2,3,4-tetrahydro-5-(2-hydroxy-3-tert.-butylaminopropoxy)-6-methoxy-isoquinoline, m.p. = 57° – 58° C. Yield: 55 percent of theory.

2-formyl-1,2,3,4-tetrahydro-6-(2-hydroxy-3-tert.-butylaminopropoxy)-7-methoxy-1-methyl-isoquinoline, m.p. = 133.5° –135.5° C. (ethyl acetate - diisopropyl ether). Yield: 80 percent of theory.

2-acetyl-1,2,3,4-tetrahydro-6-(2-hydroxy-3-tert.-butylaminopropoxy)-7-methoxy-1-methyl-isoquinoline, m.p. = 77° – 78° C. (diethyl ether). Yield: 40 percent of theory.

2-acetyl-1,2,3,4-tetrahydro-7-(2-hydroxy-3-tert.-butylaminopropoxy)-isoquinoline, m.p. = 88° –89.5° C. (ethyl acetate - diisopropyl ether). Yield: 98 percent of theory.

2-formyl-1,2,3,4-tetrahydro-6-(2-hydroxy-3-tert.-butylaminopropoxy)-7-methoxy-isoquinoline, m.p. = 114.5° – 115.5° C. (ethyl acetate - diethyl ether). Yield: 87 percent of theory.

2-acetyl-1,2,3,4-tetrahydro-6-(2-hydroxy-3-isopropylaminopropoxy)-7-methoxy-isoquinoline, m.p. = 90° –91° C. (ethyl acetate - diethyl ether) Yield: 90 percent of theory.

1,2,3,4-tetrahydro-6-(2-hydroxy-3-isopropylaminopropoxy)-7-methoxy-2-propionyl-isoquinoline, m.p. = 80° – 80.5° C. (ethyl acetate - diethyl ether). Yield: 94 percent of theory.

2-acetyl-1,2,3,4-tetrahydro-5-(2-hydroxy-3isopropylaminopropoxy)-isoquinoline, m.p. = 92° –93° C. (ethyl acetate - diisopropyl ether). Yield: 93 percent of theory.

2-acetyl-1,2,3,4-tetrahydro-5-(2-hydroxy-3-tert.-butylaminopropoxy)-isoquinoline, m.p. = 99° –100° C. (ethyl acetate - hexane. Yield: 86 percent of theory.

2-formyl-1,2,3,4-tetrahydro-5-(2-hydroxy-3-isopropylaminopropoxy)-6-methoxy-isoquinoline, m.p. = 92° –92.5° C. (ethyl acetate - diethyl ether). Yield: 93 percent of theory.

2-acetyl-1,2,3,4-tetrahydro-6-(2-hydroxy-3-isopropylaminopropoxy)-1-methyl-sioquinoline, m.p. = 99° –100° C. (ethyl acetate - diisopropyl ether). Yield: 41 percent of theory.

2-formyl-1,2,3,4-tetrahydro-6-(2-hydroxy-3-isopropylaminopropoxy)-7-methoxy-1-methyl-isoquinoline, m.p. = 110° – 111° C. (ethyl acetate - hexane). Yield: 64 percent of theory.

EXAMPLE 2

A mixture of 23.3 g of 6-(2,3-epoxy-propoxy)-2-formyl-1,2,3,4-tetrahydro-isoquinoline and 73.1 g of tertiary butylamine is held at the boiling point under reflux for 72 hours. To remove excess amine, the mixture is evaporated to dryness under reduced pressure. The crude base is obtained as a colorless oil. For conversion into the neutral mucate, the residue is heated in a tenfold amount of ethanol with one equivalent of mucic acid (10.5 g) for 30 minutes under reflux. After cooling, 34.2 g of 2-formyl-1,2,3,4-tetrahydro-6-(2-hydroxy-3-tert.butylaminopropoxy)-isoquinoline-mucate are obtained. m.p. = 173°–174.5° C. (aqueous methanol - diethyl ether).

In the same manner are prepared:

1,2,3,4-tetrahydro-6-(2-hydroxy-3-tert.-butylaminopropioxy7-methoxy-2-propionyl-isoquinoline-mucate is obtained. m.p. = 167° – 168° C. (with decomposition) (water - acetone). Yield: 91 percent of theory.

2-formyl-1,2,3,4-tetrahydro-5(2-hydroxy-3-tert.-butylaminopropoxy)-isoquinoline-mucate, m.p. = 215° – 216° C. (with decomposition) (water - acetone). Yield: 93 percent of theory.

2-formyl-1,2,3,4-tetrahydro-8-(2-hydroxy-3-tert.-butylaminopropoxy)-7-methoxy-isoquinoline-mucate, m.p. = 201°–202° C. (with decomposition) (water - acetone). Yield: 64 percent of theory.

2-acetyl-1,2,3,4-tetrahydro-8-(2-hydroxy-3-tert.-butylaminopropoxy)-7-methoxy-isoquinoline-mucate, m.p. = 182° C. (with decomposition) (aqueous methanol - ether). Yield: 43 percent of theory.

EXAMPLE 3

23.3 g. of 6-(2,3-epoxy-propoxy)-2-formyl-1,2,3,4-tetrahydroisoquinoline are held at the boiling point under reflux with 59.1 g of isopropylamine in 100 ml of isopropanol for 5 hours. The mixture is evaporated and the residue is rubbed with 150 ml of diethyl ether. 27.5 g of 2-formyl-1,2,3,4-tetrahydro-6-(2-hydroxy-3-isopropylamino-propoxy)-isoquinoline are obtained. m.p. = 56.6° – 58° C.

The hydrochloride is obtained by combining a solution of the base in isopropanol with ethanolic hydrogen chloride and adding ethyl acetate. m.p. = 147° – 148° C.

In the same manner are prepared:

2-acetyl-1,2,3,4-tetrahydro-6-(2-hydroxy-3-isopropylaminopropoxy)-isoquinoline, m.p. = 75°–76° C. (ethyl acetate - diethyl ether). Yield: 79 percent of theory. m.p. (HCl) = 120° – 121° C.

2-formyl-1,2,3,4-tetrahydro-6-(2-hydroxy-3-isopropylaminopropoxy)-7-methoxy-isoquinoline, m.p. = 100°–101° C. (ethyl acetate - diisopropyl ether). Yield: 97 percent of theory.

2-acetyl-1,2,3,4-tetrahydro-6-(2-hydroxy-3-isopropylaminopropoxy)-7-methoxy-1-isoquinoline, m.p. 123.5° – 124.5° C. (ethyl acetate - diisopropyl ether). Yield: 89 percent of theory.

2-formyl-1,2,3,4-tetrahydro-5-(2-hydroxy-3-isopropylaminopropoxy)-isoquinoline, m.p. = 50°–51° C. (diethyl ether). Yield: 77 percent of theory. m.p. mucate = 104°–105° C. (methanol - diethyl ether).

EXAMPLE 4

The residue from (B. b) is heated with 59.1 g of isopropylamine and 100 ml of methanol for 10 hours in a autoclave at 100° C. After evaporation to dryness under reduced pressure, the residue is rubbed with diethyl ether. After recrystallization of the crude product from ethyl acetate - diethyl ether, 8.9 g of 2-acetyl-1,2,3,4-tetrahydro-6-(2-hydroxy-3-isopropylaminopropoxy)-7-methoxy-isoquinoline are obtained. m.p. = 89°–90° C.

EXAMPLE 5

Tablets of the following composition were formed on a tablet press in the usual fashion:

20.00 mg of 2-acetyl-1,2,3,4-tetrahydro-6-(2-hydroxy-3-isopropylamino-propoxy)-isoquinoline
100.00 mg of cornstarch
9.00 mg of gelatin
30.00 mg of lactose
15.00 mg of talc
1.50 mg of chemically pure silicic acid in a submicroscopically fine state of division ("Aerosil")
4.50 mg of potato starch (as a 6 percent paste).

EXAMPLE 6

Dragees of the following composition were prepared in the usual fashion:

2.00 mg of 2-formyl-1,2,3,4-tetrahydro-5-(2-hydroxy-3-isopropylamino-propoxy)-isoquinoline
50.00 mg of core mass
40.00 mg of sugaring mass.

The core comprises 9 parts of cornstarch, 3 parts of Lactose, and 1 part of a 60:40 vinyl pyrrolidone-vinyl acetate copolymer ("Luviskol VA 64") (cf. Pharm. Ind. 1962, 586). The sugaring mass comprises 5 parts of cane sugar, 2 parts of cornstarch, 2 parts of calcium carbonate, and 1 part of talc. The dragees prepared in this manner were subsequently provided with a coating resistant to stomach juices.

EXAMPLE 7

5.0 g of 2-acetyl-1,2,3,4-tetrahydro-6-(2-hydroxy-3-isopropylamino-propoxy)-7-methoxy-isoquinoline are dissolved in 2.0 liters of water. The solution is brought to a pH of 7.0 with hydrochloric acid, is adjusted isotonically with sodium chloride, and is sterilely filled into ampules of 2 ml capacity.

What is claimed is:

1. An isoquinoline compound of the formula

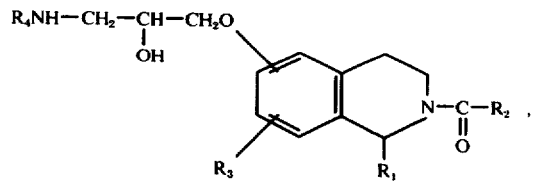

and salts thereof with physiologically tolerable acids, wherein $R_1$ is hydrogen or methyl, $R_2$ is hydrogen or lower alkyl, $R_3$ is hydrogen or methoxy, and $R_4$ is isopropyl or tertiary butyl.

2. The compound as in claim 1 which is 2-formyl-1,2,3,3-tetrahydro-6-(2-hydroxy-3-tert.-butylamino-propoxy)-isoquinoline.

3. The compound as in claim 1 which is 2-formyl-1,2,3,4-tetrahydro-6-(2-hydroxy-3-isopropyl-amino-propoxy)-isoquinoline.

4. The compound as in claim 1 which is 2-acetyl-1,2,3,4-tetrahydro-6-(2-hydroxy-3-isopropyl-amino-propoxy)-isoquinoline.

5. The compound as in claim 1 which is 2-acetyl-1,2,3,4-tetrahydro-6-(2-hydroxy-3-tert.-butylamino-propoxy)-isoqunioline.

6. The compound as in claim 1 which is 2-formyl-1,2,3,4-tetrahydro-(6-(2-hydroxy-3-isopropyl-amino-propoxy)-7-methoxyisoquinoline.

7. The compound as in claim 1 which is 2-formyl-1,2,3,4-tetrahydro-6-(2-hydroxy-3-tert.-butyl-amino-propoxy)-7-methoxyisoquinoline.

8. The compound as in claim 1 which is 2-acetyl-1,2,3,4-tetrahydro-6-(2-hydroxy-3-isopropyl-amino-propoxy)-7-methoxyisoquinoline.

9. The compound as in claim 1 which is 2-acetyl-1,2,3,4-tetrahydro-6-(2-hydroxy-3-tert.-butylamino-propoxy)-7-methoxyisoquinoline.

10. The compound as in claim 1 which is 1,2,3,4-tetrahydro-6-(2-hydroxy-3-isopropylamino-propoxy)-7-methoxy-2-propionylisoquinoline.

11. The compound as in claim 1 which is 1,2,3,4-tetrahydro-6-(2-hydroxy-3-tert.-butylamino-propoxy)-7-methoxy-2-propionylisoquinoline.

12. The compound as in claim 1 which is 2-acetyl-1,2,3,4-tetrahydro-6-(2-hydroxy-3-isopropyl-amino-propoxy)-7-methoxy-1-methyl-isoquinoline.

13. The compound as in claim 1 which is 2-formyl-1,2,3,4-tetrahydro-5-(2-hydroxy-3-isopropyl-amino-propoxy)-isoquinoline.

14. The compound as in claim 1 which is 2-formyl-1,2,3,4-tetrahydro-5-(2-hydroxy-3-tert.-butylamino-propoxy)-isoquinoline.

15. The compound as in claim 1 which is 2-acetyl-1,2,3,4-tetrahydro-5-(2-hydroxy-3-isopropyl-amino-propoxy)-isoquinoline.

16. The compound as in claim 1 which is 2-acetyl-1,2,3,4-tetrahydro-5-(2-hydroxy-3-tert.-butylamino-propoxy)-isoquinoline.

17. The compound as in claim 1 which is 2-formyl-1,2,3,4-tetrahydro-5-(2-hydroxy-3-isopropyl-amino-propoxy)-6-methoxyisoquinoline.

18. The compound as in claim 1 which is 2-formyl-1,2,3,4-tetrahydro-5-(2-hydroxy-3-tert.-butylamino-propoxy)-6-methoxyisoquinoline.

19. The compound as in claim 1 which is 2-acetyl-1,2,3,4-tetrahydro-5-(2-hydroxy-3-tert.-butylamino-propoxy)-6-methoxyisoquinoline.

20. The compound as in claim 1 which is 2-acetyl-1,2,3,4-tetrahydro-6-(2-hydroxy-3-isopropyl-amino-propoxy)-1-methylisoquinoline.

21. The compound as in claim 1 which is 2-formyl-1,2,3,4-tetrahydro-6(2-hydroxy-3-isopropyl-amino-propoxy)-7-methoxy-1-methyl-isoquinoline.

22. The compound as in claim 1 which is 2-formyl-1,2,3,4-tetrahydro-6-(2-hydroxy-3-tert.-butylamino-propoxy)-7;1-methoxy-1-methyl-isoquinoline.

23. The compound as in claim 1 which is 2-acetyl-1,2,3,4tetrahydro-6-(2-hydroxy-3-tert.-butylamino-propoxy)-7-methoxy-1-methyl-isoquinoline.

24. The compound as in claim 1 which is 2-acetyl-1,2,3,4-tetrahydro-7-(2-hydroxy-3-tert.-butylamino-propoxy)-isoquinoline.

25. The compound as in claim 1 which is 2-formyl-1,2,3,4-tetrahydro-8-(2-hydroxy-3-tert.-butylamino-propoxy)-7-methoxy-isoquinoline.

26. The compound as in claim 1 which is 2-acetyl-1,2,3,4-tetrahydro-8(2-hydroxy-3-tert.-butylamino-propoxy)-7-methoxy-isoquinoline.

27. A pharmaceutical composition for the treatment of functional heart ailments or hypertonia, which composition comprises an effective amount of a compound as in claim 1 in admixture with a pharmaceutical excipient.

* * * * *